United States Patent [19]

Allegretto et al.

[11] Patent Number: 5,585,244
[45] Date of Patent: Dec. 17, 1996

[54] DETECTION OF RETINOID X RECEPTOR SUBTYPE γ PROTEINS

[75] Inventors: Elizabeth A. Allegretto, La Jolla; J. Wesley Pike, Encinitas, both of Calif.

[73] Assignee: Ligand Pharmaceuticals Incorporated, San Diego, Calif.

[21] Appl. No.: 258,851

[22] Filed: Jun. 10, 1994

[51] Int. Cl.$^6$ .............................. G01N 33/53; C07K 16/18
[52] U.S. Cl. .................. 435/7.1; 530/387.1; 530/387.9; 530/388.1; 530/388.2; 530/388.22; 530/389.1; 435/7.2; 435/7.21; 435/7.23
[58] Field of Search .......................... 435/7.1, 7.2, 7.21, 435/7.23; 436/63, 16 H, 501; 530/387.1, 387.9, 388.1, 388.2, 388.22, 389.1

[56] References Cited

U.S. PATENT DOCUMENTS

| | | | |
|---|---|---|---|
| 5,234,962 | 8/1993 | de Grave et al. | 521/57 |
| 5,246,962 | 9/1993 | Chandraratna | 514/438 |
| 5,264,578 | 11/1993 | Chandraratna | 546/269 |

FOREIGN PATENT DOCUMENTS

| | | |
|---|---|---|
| 2081990 | 11/1993 | Canada . |
| 9311755 | 12/1991 | WIPO . |
| 9321146 | 4/1993 | WIPO . |

OTHER PUBLICATIONS

Reichrath et al "Immunohistological detection of retinoid–X receptor (RXR–a,b,g) expression in normal and psoriatic human skin" J. Invest. Dermatol. vol. 101, Abstract No. 358, p. 447 Sep. 3, 1993.

Allegretto, et al., "Transactivation Properties of Retinoic Acid and Retinoid X Receptors in Mammalian Cells and Yeast: Correlation With Hormone Binding and Effects of Metabolism" *J Biol Chem* 268:26625–26633 (1993).

Allegretto, et al., "Immunochemical Detection of Unique Proteolytic Fragments of the Chick 1,25–Dihydroxyvitamin D$_3$ Receptor" *J. Biol. Chem.* 262:1312–1319 (1987).

Allenby, et al., "Retinoic Acid Receptors and Retinoid X Receptors: Interactions With Endogenous Retinoic Acids" *Proc. Natl. Acad. Sci. USA* 90:30–34 (1993).

Benbrook, et al., "A New Retinoic Acid Receptor Identified From a Hepatocellular Carcinoma" *Nature* 333:669–672 (1988).

Blomhoff et al., "Transport and Storage of Vitamin A" *Science* 250:399–404 (1990).

Daly et al., "Nuclear Retinoic Acid Binding Proteins and Receptors in Retinoic Acid Responsive Cell Lines" *Exp. Cell. Biol.* 57:339–345 (1989).

Dawson et al., "Preparation of 9–cis–Retinoic Acid [11, 12–$^3$H(N)] by Photochemical Isomerization" *J. Labelled Compd. Radiopharm.*, 33:245 (1993).

Gaub et al., "Antibodies Specific to the Retinoic Acid Human Nuclear Receptors Alpha and Beta" *Proc. Natl. Acad. Sci. USA* 86:3089–3093 (1989).

Gaub et al., "Immunodetection of Multiple species of Retinoic Acid Receptor α: Evidence for Phosphorylation" *Experi. Cell Res.* 201:335–346 (1992).

Giguere, "Retinoic Acid Receptors and Cellular Retinoid Binding Proteins: Complex Interplay in Retinoid Signalling" *Endocrine Reviews* 15:in press (1994).

Giguere, et al., "Identification of a Receptor for the Morphogen Retinoic Acid" *Nature* 330:624–629 (1987).

Giovanella, et al., "Heterotransplantation of Human Malignant Tumors in Nude Thymusless Mice II. Malignant Tumors Induced by Injection of Cell Cultures Derived From Human Solid Tumors" *JNCI* 52:921–927 (1974).

Hashimoto et al., "Expression of Retinoic Acid Receptor Genes and the Ligand–Binding Selectivity of Retinoic Acid Receptors (RARs)" *Biochem. Biophys. Res. Comm.* 166:1300–1307 (1990).

Heyman et al., "9–Cis Retinoic Acid is a High Affinity Ligand for the Retinoid X Receptor" *Cell* 68:397–406 (1992).

Ishikawa et al., "A Functional Retinoic Acid Receptor Encoded by the Gene on Human Chromosome 12" *Mol Endocrinol.* 4:837–844 (1990).

Kaegi and DeGraw "Preparation of All Trans–Retinoic–11–$^3$H Acid and All Trans–Retinyl–11–$^3$H Acetate" *J. Labelled Compd. Radiopharm.*, 18:1099 (1981).

Kohler and Milstein, "Continuous Cultures of Fused Cells Secreting Antibody of Predefined Specificity" *Nature* 256:495–497 (1975).

Largman et al., "Expression of Retinoic Acid Receptor Alpha mRNA in Human Leukemia Cells" *Blood* 74:99–102 (1989).

Leid et al., "Purification, Cloning and RXR Identity of the HeLa Cell Factor With Which RAR or TR Heterodimerizes to Bind Target Sequences Efficiently" *Cell* 68:377–395 (1992).

Levin et al., "9–Cis Retinoic Acid Stereoisomer Binds and Activates the Nuclear Receptor RXRα" *Nature* 355:359–361 (1992).

Lippman et al., "13–Cis Retinoic Acid Plus Interferon Alpha–2a: Highly Active Systemic Therapy for Squamous Cell Carcinoma of the Cervix" *J. Natl. Cancer Inst.* 84:241–245 (1992).

Mangelsdorf et al., "A Direct Repeat in the Cellular Retinol–Binding Protein Type II Gene confers Differential Regulation by RXR and RAR" *Cell*, 66:555–61 (1991).

(List continued on next page.)

*Primary Examiner*—Toni R. Scheiner
*Assistant Examiner*—Yvonne Eyler
*Attorney, Agent, or Firm*—Lyon & Lyon

[57] ABSTRACT

The present invention features peptides derived from RXRX, and antibodies elicited by the peptides. These antibodies bind specifically to RXRX subtypes in its native, functional conformation. Methods are disclosed for detection of RXRX with the antibodies in immunological assays. In addition, this invention describes a hormone-binding immunoprecipitation assay which utilizes both the retinoid receptor subtype specific antibodies and retinoid receptor ligands to detect and measure RXR and RAR subtypes in a sample. A method is also disclosed for determining the profile of retinoid receptor subfamily members with the retinoid receptor ligands.

11 Claims, 8 Drawing Sheets

OTHER PUBLICATIONS

Mangelsdorf et al., "Characterization of Three RXR Genes That Mediate the Action of 9-Cis Retinoic Acid" *Genes Develop.* 6:329-344 (1992).

Mangelsdorf, Umesono, and Evans, "Retinoid Receptors," In: Sporn M B, Roberts A B, and Goodman D S (eds) *The Retinoids: Biology, Chemistry, and Medicine* Raven Press, pp. 319-349 (1994).

Mangelsdorf et al., "Nuclear Receptor That Identifies a Novel Retinoic Acid Response Pathway" *Nature* 345:224-229 (1990).

Marks et al., "H-2RIIBP Expressed from a Baculovirus Vector Binds to Multiple Hormone Response Elements" *Mole. Endocrio.* 9:219 (1992).

Nervi et al., "Identification and Characterization of Nuclear Retinoic Acid-Binding Activity in Human Myeloblastic Leukemia HL-60 Cells" Proc. Natl. Acad. Sci. USA 86:5854-5858 (1989).

Rochette-Egly et al., "Retinoic Acid Receptor-β: Immunodetection and Phosphorylation on Tyrosine Residues" *Mole. Endocri.* 6:2197-2209 (1992).

Rochette-Egly et al., "Retinoic Acid Receptor τ: Specific Immunodetection and Phosphorylation" *J. Cell Bio.*, 115:535-545, (1991).

Roman et al., "Estradiol Induction of Retinoic Acid Receptors in Human Breast Cancer Cells" *Cancer Res.* 53:5940-5945 (1993).

van der Burg et al., "Retinoic Acid Resistance of Estradiol-Independent Breast Cancer Cells Coincides with Diminished Retinoic Acid Receptor Function" *Mol Cell Endocrinol* 91:149-157 (1993).

Warrell et al., "Differentiation Therapy of Acute Promelocytic Leukemia with Tretinoin (All-Trans Retinoic Acid)" *N. Engl. J. Med.* 324:1385-1393 (1991).

White et al., "All-Trans Retinoic Acid in the Treatment of Acute Promelocytic Leukemia" Aust. NZ. J. Med. 22:449-455 (1992).

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 16 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 1:

Asp Arg Asn Glu Asn Glu Val Glu Ser Thr Ser Ser Ala Asn
1               5                       10

Glu Asp
15

( 2 ) INFORMATION FOR SEQ ID NO: 2:

( i ) SEQUENCE CHARACTERISTICS:
        ( A ) LENGTH: 13 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 2:

Gln Arg Gly Lys Asp Arg Asn Glu Asn Glu Val Glu Cys
1               5                   10

( 2 ) INFORMATION FOR SEQ ID NO: 3:

( i ) SEQUENCE CHARACTERISTICS:
        ( A ) LENGTH: 14 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 3:

Gln Lys Ser Asp Gln Gly Val Glu Gly Pro Gly Ala Thr Cys
1               5                   10

( 2 ) INFORMATION FOR SEQ ID NO: 4:

( i ) SEQUENCE CHARACTERISTICS:
        ( A ) LENGTH: 14 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 4:

Arg Gln Arg Ser Arg Glu Arg Ala Glu Ser Glu Ala Glu Cys
1               5                   10

( 2 ) INFORMATION FOR SEQ ID NO: 5:

( i ) SEQUENCE CHARACTERISTICS:
        ( A ) LENGTH: 13 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 5:

Gly Leu Ala Pro Pro Pro Gly Ser Cys Ser Pro Ser Cys
1               5                   10

( 2 ) INFORMATION FOR SEQ ID NO: 6:

( i ) SEQUENCE CHARACTERISTICS:
        ( A ) LENGTH: 14 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:

( x i ) SEQUENCE DESCRIPTION: SEQ ID NO: 6:

Val Glu Asn Ser Gly Val Ser Gln Ser Pro Leu Val Gln Cys
1               5                   10

( 2 ) INFORMATION FOR SEQ ID NO: 7:

(  i  ) SEQUENCE CHARACTERISTICS:
  ( A ) LENGTH: 14 AMINO ACIDS
  ( B ) TYPE: AMINO ACID
  ( D ) TOPOLOGY: LINEAR ( i i ) MOLECULE TYPE: PEPTIDE ( i x ) FEATURE:
  ( D ) OTHER INFORMATION:

( x i ) SEQUENCE DESCRIPTION: SEQ ID NO: 7:

```
Asp Glu Val Pro Gly Gly Gln Gly Lys Gly Gly Leu Lys Cys
 1               5                  10
```

( 2 ) INFORMATION FOR SEQ ID NO: 8:

(  i  ) SEQUENCE CHARACTERISTICS:
  ( A ) LENGTH: 16 AMINO ACIDS
  ( B ) TYPE: AMINO ACID
  ( D ) TOPOLOGY: LINEAR ( i i ) MOLECULE TYPE: PEPTIDE ( i x ) FEATURE:
  ( D ) OTHER INFORMATION:

( x i ) SEQUENCE DESCRIPTION: SEQ ID NO: 8:

```
Ser Pro Gly Gln Ile Leu Asp Phe Tyr Thr Ala Ser Pro Ser
 1               5                  10
Ser Cys
 15
```

( 2 ) INFORMATION FOR SEQ ID NO: 9:

(  i  ) SEQUENCE CHARACTERISTICS:
  ( A ) LENGTH: 13 AMINO ACIDS
  ( B ) TYPE: AMINO ACID
  ( D ) TOPOLOGY: LINEAR ( i i ) MOLECULE TYPE: PEPTIDE ( i x ) FEATURE:
  ( D ) OTHER INFORMATION:

( x i ) SEQUENCE DESCRIPTION: SEQ ID NO: 9:

```
Gln Lys Ser Asp Gln Gly Val Glu Gly Pro Gly Gly Thr
 1               5                  10
```

DETECTION OF RETINOID X RECEPTOR SUBTYPE γ PROTEINS

FIELD OF THE INVENTION

This invention relates to retinoid receptor antibodies. This invention also relates to the detection of retinoid receptors in a sample.

BACKGROUND OF THE INVENTION

The vitamin A metabolite retinoic acid has been recognized as inducing a broad spectrum of biological effects. A variety of structural analogues of retinoic acid have been synthesized that also have been found to be bioactive. Some, such as Retin-A® (registered trademark of Johnson & Johnson) and Accutane® (registered trademark of Hoffmann-LaRoche), have found utility as therapeutic agents for the treatment of various pathological conditions. Metabolites of vitamin A and their synthetic analogues are collectively herein called "retinoids". Synthetic retinoids have been found to mimic many of the pharmacological actions of retinoic acid. However, the broad spectrum of pharmacological actions of retinoic acid is not reproduced in full by all bioactive synthetic retinoids.

Medical professionals are interested in the medicinal applications of retinoids. Among their uses approved by the FDA is the treatment of severe forms of acne and psoriasis. Evidence also exists that these compounds can be used to arrest and, to an extent, reverse the effects of skin damage arising from prolonged exposure to the sun. Other evidence indicates that these compounds may be useful in the treatments of a variety of cancers including melanoma, cervical cancer, some forms of leukemia, and basal and squamous cell carcinomas. Retinoids have also been shown to be efficacious in treating premalignant cell lesions, such as oral leukoplakia, and to prevent the occurrence of malignancy.

Retinoids regulate the activity of two distinct intracellular receptor subfamilies; the retinoic acid receptors (RARs) and the retinoid X receptors (RXRs). The RAR and RXR subfamilies are divided into six subtypes, based upon their primary sequence homology, their ability to bind to various retinoid analogues, and by their promoter recognition sequence specificity (Mangelsdorf D. J., Umesono K., and Evans R. M. 1994 Retinoid receptors. In: Sporn M. B., Roberts A. B., and Goodman D. S. (eds) The Retinoids: Biology, Chemistry, and Medicine. Raven Press, pp 319–349; Giguere V. 1994, Retinoic acid receptors and cellular retinoid binding proteins: complex interplay in retinoid signalling. Endocrine Reviews 15:in press). The RARs have three subtypes denoted α, β, and γ. The RXRs also have three known subtypes, α, β, and γ.

RARs and RXRs differ in several aspects. First, the RARs and RXRs are divergent in primary structure (e.g., the ligand binding domains of RARα and RXRα have approximately 27% amino acid identity). These structural differences are reflected in the different relative degrees of responsiveness of RARs and RXRs to various vitamin A metabolites and synthetic retinoids. RARs bind to both 9-cis retinoic acid (9cRA) and all-trans retinoic acid (tRA) with equally high affinity, displaying $K_d$ values of 0.2–0.8 nM (Allenby G., et al., 1993, "Retinoic acid receptors and retinoid X receptors: interactions with endogenous retinoic acids." Proc Natl Acad Sci USA 90:30–34; Allegretto E. A., et al., 1993, "Transactivation properties of retinoic acid and retinoid X receptors in mammalian cells and yeast: correlation with hormone binding and effects of metabolism." J Biol Chem 268:26625–26633). RXRs bind with high affinity and specificity to 9cRA (Levin A. A., et al., 1992, 9-cis retinoic acid stereoisomer binds and activates the nuclear receptor RXRα. Nature 355:359–361; Heyman R. A., et al., 1992, 9-cis retinoic acid is a high affinity ligand for the retinoid X receptor. Cell 68:397–406) with $K_d$ values of 1–2 nM (Allegretto EA, et al., 1993, "Transactivation properties of retinoic acid and retinoid X receptors in mammalian cells and yeast: correlation with hormone binding and effects of metabolism." J Biol Chem 268:26625–26633), but do not bind to tRA ($IC_{50}$ >50,000 nM versus tritiated 9 cRA (Allenby G., et al., 1993, "Retinoic acid receptors and retinoid X receptors: interactions with endogenous retinoic acids." Proc Natl Acad Sci USA 90:30–34; Allegretto E. A., et al , 1993, "Transactivation properties of retinoic acid and retinoid X receptors in mammalian cells and yeast: correlation with hormone binding and effects of metabolism." J Biol Chem 268:26625–26633)). In addition, distinctly different patterns of tissue distribution are seen for RARs and RXRs. For example, in contrast to the RARs, which are not expressed at high levels in the visceral tissues, RXRα mRNA has been shown to be most abundant in the liver, kidney, lung, muscle and intestine. Furthermore, RARs and RXRs have different target gene specificity. For example, response elements in cellular retinol binding protein type II (CRBPII) and apolipoprotein AI genes confer responsiveness to RXR, but not to RAR. RAR has also been shown to repress RXR-mediated activation through the CRBPII RXR response element (Mangelsdorf et al., Cell, 66:555–61 (1991)).

Gaub, M. P., et al., Proc. Natl. Acad. Sci. USA., 86:3089–3093, (1989) used synthetic peptides to generate anti-RARα and anti-RARβ antisera and used these antisera to identify RARα and RARβ expressed in HL-60 cells.

Rochette-Egly, C., et al., J. Cell Bio., 115(2):535–545, (1991) used synthetic peptides to generate anti-RARγ 1 antibodies which were used to detect mRARγ 1 and mRARγ 2.

Gaub, M. P., et al., Experi. Cell Res., 201(2)335–346, (1992) used synthetic peptides or fusion proteins to generate human and mouse RARe 1 antibodies.

Rochette-Egly, C., et al., Mole. Endocri., 6(12):2197–2209, (1992) used synthetic peptides or fusion proteins to generate human and mouse RARβ antibodies.

Heyman, R. A., et al., Cell, 68:397–406, 1992, used an hRXRα antiserum in Western blot analysis. The antibody "was a rabbit polyclonal serum raised against a synthetic peptide corresponding to amino acids 214–229 (DRNENEVESTSSANED) of hRXRα." Id. at 405.

Marks, M. S., et al., Mole. Endocrio., 9(2):219, (1992) made an antipeptide antibody that reacts with the recombinant H-2RIIBP and used the antibody in Western blot analysis.

SUMMARY OF THE INVENTION

The present invention relates to immunogenic peptides and use of these peptides for the generation of antibodies which bind selectively to each of the retinoid receptor subtypes. This invention also relates to antibodies that specifically bind to a retinoid receptor subtype, i.e., RARα, RARβ, RARγ, RXRα, RXRβ, and RXRγ. These antibodies bind to the retinoid receptors in their native and functional state (i.e., capable of binding to ligand).

In addition, this invention relates to methods for determining the levels of retinoid receptor proteins in a sample.

One method uses the differential binding affinity of various ligands for their respective retinoid receptors to determine the profile of retinoid receptor subfamily members that are present in the sample. In an example, a hormone-binding assay makes use of an RAR-selective ligand, RXR-selective ligand, and retinoid receptor selective ligand to determine the levels of RARs and RXRs in a sample.

By "ligand" is meant a compound that binds in a saturable, high affinity and specific manner to an intracellular protein to elicit a functional response, including, but not limited to retinoids. The ligands applicable to this invention include, but are not limited to, tRA, 9cRA and LG100268(2-[1-(3,5,5,8,8,-pentamethyl-5,6,7,8-tetrahydro-2-naphthyl)-cyclopropyl]-pyridine-5-carboxylic acid, disclosed in PCT publication WO93/21146, Oct. 28, 1993, incorporated by reference herein). RAR selective ligands are disclosed in U.S. Pat. Nos. 5,264,578, 5,246,962 and 5,234,926, incorporated by reference herein. Retinoid receptor selective ligands are disclosed in PCT publication WO93/11755, Jun. 24, 1993, incorporated by reference herein.

By "sample" is meant cells, extracts of cells, or biological fluids such as, but not limited to, blood, serum, plasma, or urine. Any cell or tissue can be used as a sample, however the most preferred samples are obtained from tumor cells.

Another method is an immunoprecipitation assay that exploits the receptor subtype-specific antibodies that were generated against peptide sequences encoded by the retinoid receptor subtypes. The combination of the hormone-binding assay and the immunoprecipitation assay yields a result that is much more accurate and informative than either assay provides alone.

Thus, in one aspect, this invention features immunogenic peptides capable of eliciting antibodies that are specific to a retinoid X receptor subtype, e.g., RXRα, RXRβ or RXRγ. The peptides (excluding the synthetic peptide corresponding to amino acids 214–229 of hRXRα, i.e., DRNENEVESTSSANED Seq. ID. No. 1) are selected from a region of the receptor that is likely to be exposed and therefore antigenic, such as, but not limited to, the hinge regions of the RXRs. The sequence of a peptide is chosen to be unique to an RXR subtype and substantially nonhomologous to amino acid sequences of other RXR subtypes. By substantially nonhomologous is meant that the antibody elicited by said peptide reacts with the subtype from which the peptide is derived but does not cross-react with other RXR subtypes to an extent which would not allow one of ordinary skill in the art to differentiate between them. In addition to using the peptides in their original sequence and chemical structure, the peptides may be extended or modified without depleting its antigenic property by methods known to those skilled in the art.

In a preferred embodiment, the immunogenic peptide comprises a segment of a hinge region of a retinoid X receptor.

In another preferred embodiment, the peptide has 8 to 30 amino acid residues. In a further preferred embodiment, the peptide has 12 amino acid residues.

In a third preferred embodiment, an immunogenic peptide is selected from a hinge region of RXRα.

In a fourth preferred embodiment, an immunogenic peptide is selected from a hinge region of RXRβ.

In a fifth preferred embodiment, an immunogenic peptide is selected from a hinge region of RXRγ.

By "hinge region" of an intracellular receptor, also referred to as "domain D", is meant the region of the receptor between the DNA-binding domain (C domain) and hormone-binding domain (E domain). For example, a hinge region for RXRα extends from amino acid 200 to amino acid 225.

The most preferred peptide for generating RXR antibodies are as follows: QRGKDRNENEVEC Seq. ID No. 2 (derived from RXRα), QKSDQGVEGPGATC Seq. ID No. 3 (derived from RXRβ), and RQRSRERAESEAEC Seq. ID No. 4 (derived from RXRγ).

In a second aspect, this invention features immunogenic peptides capable of eliciting antibodies to retinoic acid receptor subtypes, including, GLAPPPGSCSPSC Seq. ID No. 5 (derived from RARα), VENSGVSQSPLVQC Seq. ID No. 6 (derived from RARβ), and DEVPGGQGKGGLKC Seq. ID No. 7 (derived from RARγ).

In a third aspect, this invention features a retinoid receptor subtype specific antibody elicited by a peptide disclosed above. This antibody binds both to the peptide and a retinoid receptor subtype.

In a preferred embodiment, the retinoid receptor subtype-specific antibody is a polyclonal antibody.

In another preferred embodiment, the retinoid receptor subtype-specific antibody is a monoclonal antibody.

Polyclonal and monoclonal antibodies may be prepared by standard techniques known to those skilled in the art, including, but not limited to, the disclosure of Canadian application no. (A1) 2,081,990, incorporated by reference herein.

In yet another preferred embodiment, the retinoid receptor subtype-specific antibody is able to detect functional retinoid receptor, i.e., a receptor capable of binding to a ligand. The antibody is able to bind to a ligand-bound retinoid receptor.

In a fourth aspect, this invention features a method for detection of a retinoid receptor subtype in a sample. Basically, the method comprises incubating a sample with an antibody described above and assaying for sample constituent bound to the antibody.

Incubating conditions depend on the format employed in the assay, the detection methods employed, and the type and nature of the antibody used in the assay. One skilled in the art will recognize that any one of the commonly available immunological assay formats (such as, but not limited to, radioimmunoassays, enzyme-linked immunosorbent assays, immunoblotting, immunoprecipitation, and immunocytochemistry) can readily be adapted to employ the antibodies of the present invention. Examples of such assays can be found in Chard, T. "*An Introduction to Radioimmunoassay and Related Techniques*" Elsevier Science Publishers, Amsterdam, The Netherlands (1986); Bullock, G. R. et al, "*Techniques in Immunocytochemistry,*" Academic Press, Orlando, Fla. Vol. 1 (1982), Vol. 2 (1983), Vol. 3 (1985); and Tijssen, P., "*Practice and Theory of Enzyme immunoassays; Laboratory Techniques in Biochemistry and Molecular Biology,*" Elsevier Science Publishers, Amsterdam, The Netherlands (1985), incorporated by reference herein.

The sample used in the above-described method will vary based on the assay format, nature of the detection method and the tissues, cells or extracts used as the sample to be assayed. Methods for preparing cell extracts are well known in the art and can be readily adapted in order to obtain a sample which is capable with the system utilized.

This method is able to identify both denatured retinoid receptor subtypes and functional retinoid receptor subtypes such as a ligand-bound retinoid receptor subtype.

In a fifth aspect, this invention features a method for identifying the level of a retinoid receptor subtype in a sample that utilizes both antibody-receptor interaction and ligand-receptor interaction. In this method, a sample is contacted with both a retinoid receptor subtype-specific antibody and a detectable ligand that binds to the retinoid receptor subtype. The level of the retinoid receptor subtype is measured by the amount of the detectable ligand bound to the antibody-receptor complex.

In a preferred embodiment, the detectable ligand is labeled with a radioactive element, such as, but not limited to, tritium.

In a sixth aspect, this invention features a method for identifying the level of a group of retinoid binding proteins in a sample that utilizes a detectable group specific ligand. A group specific ligand is one that binds to one group of retinoid binding proteins but not to at least one other group. The level of a group of retinoid binding proteins is measured by the amount of the detectable group specific ligand bound to the group. tRA, 9CRA and LG100268 are specific, nonlimiting examples of group specific ligands. The groups identified by this method include, but are not limited to, retinoic acid receptor subfamily, retinoid X receptor subfamily and cellular retinoic acid binding proteins.

In a preferred embodiment, the level of RAR subfamily in a sample is measured by the difference of detectable tRA complexed to the sample in the absence and presence of an excess amount of 9CRA.

In another preferred embodiment, the level of RAR subfamily in a sample is measured by the difference of detectable 9cRA complexed to the sample in the absence and presence of an excess amount of tRA.

In a third preferred embodiment, the level of RXR subfamily in a sample is measured by the difference of detectable 9cRA complexed to the sample in the absence and presence of an excess amount of LG100268 or other RXR selective compound.

In a fourth preferred embodiment, the level of combined RAR subfamily and RXR subfamily in a sample is measured by the difference of detectable 9cRA-complexed to the sample in the absence and presence of an excess amount of undetectable 9cRA.

The detection methods of this invention are useful in the development of therapeutic strategies for certain diseases by assessment of which receptor subfamily or which receptor subtypes are present and consequent administration of the appropriate receptor subtype-selective drugs. For example, the determination of retinoid receptors in a given tumor and whether those receptors are functional (i.e., capable of binding to ligands), facilitates the selection of receptor-specific compounds for the treatment of cancerous growth. Those skilled in the art can correlate such drugs to RXR or RAR phenotype.

Other features and advantages of the invention will be apparent from the following detailed description of the invention, and from the claims.

DETAILED DESCRIPTION OF THE INVENTION

Figure 1A:
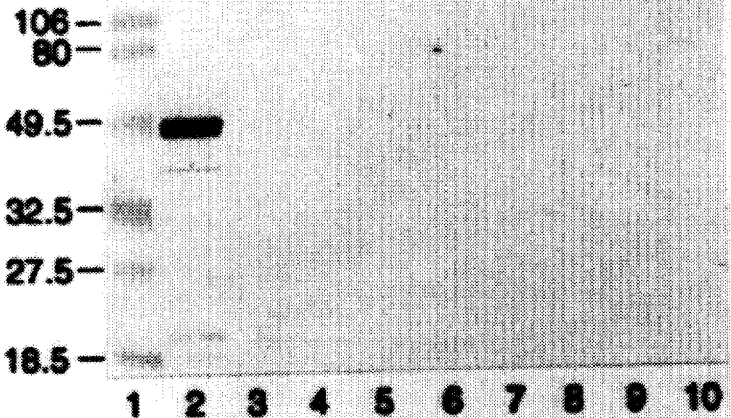
FIG. 1 shows immunoblot analysis and crossreactivity study of anti-retinoid receptor antibodies. Extracts from cells expressing a solitary recombinant retinoid receptor were electrophoresed on SDS-PAGE gels, transferred to nitrocellulose membranes and probed with antibodies against RARα (A), RARβ (B), RARγ (C), RXRα (D), RXRβ (E), or RXR₇ (F).
Figure 1B:
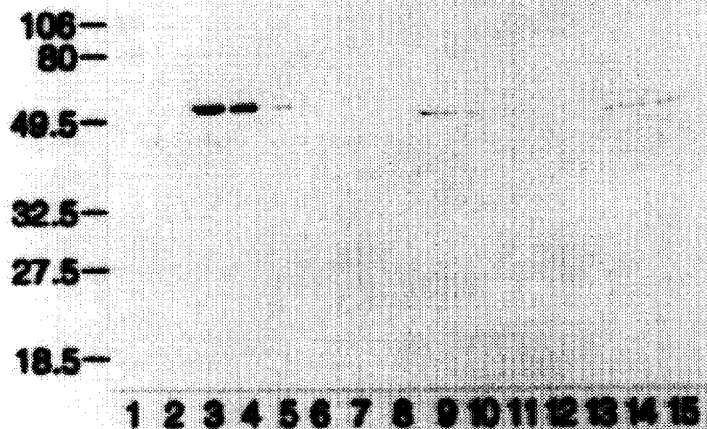
Figure 1C:
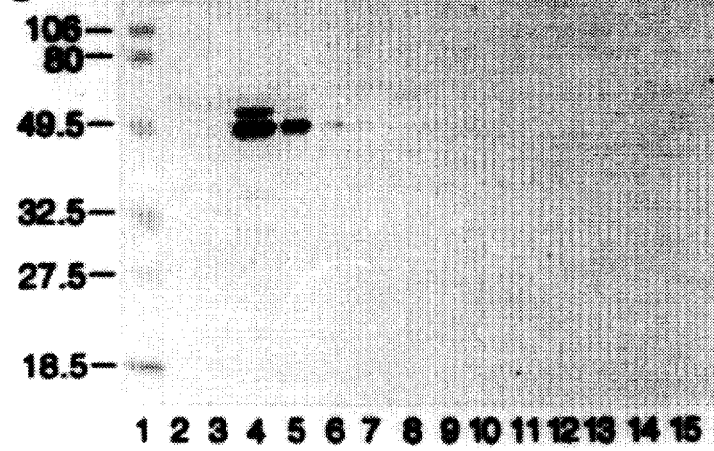
Figure 1D:
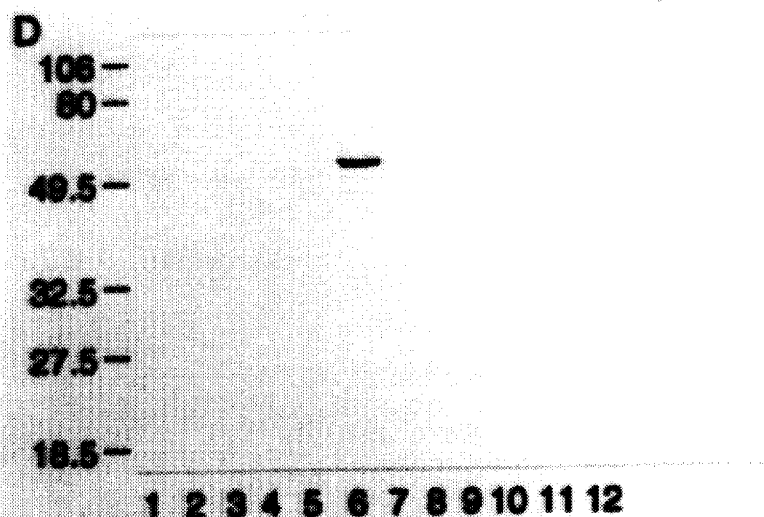
Figure 1E:
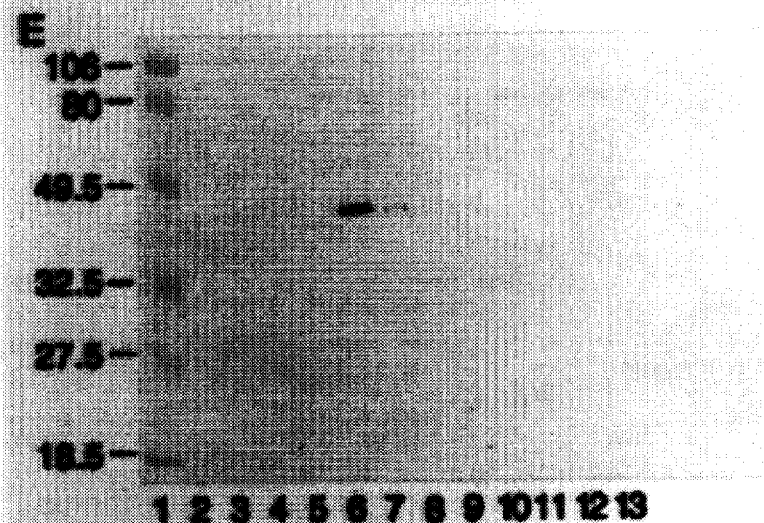
Figure 1F:
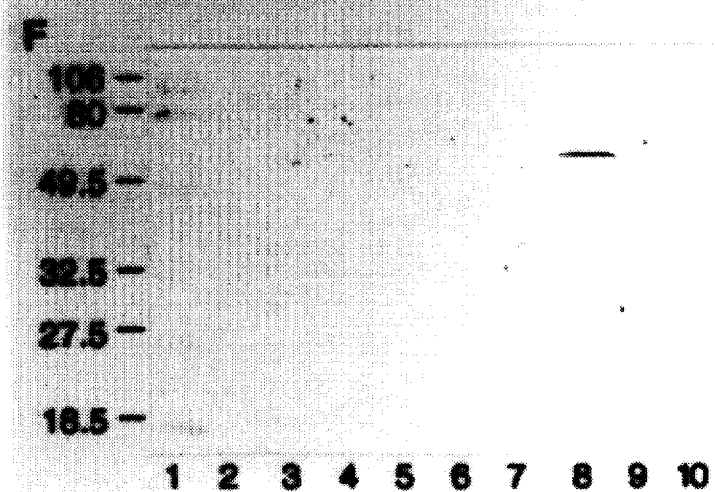

There are a number of disease conditions that respond to treatment with retinoids, such as leukemia (Warrell R. P., et al., 1991 Differentiation therapy of acute promelocytic leukemia with tretinoin (all-trans retinoic acid). N Engl J Med 324:1385–1393; White K. L., et al., 1992 All-trans retinoic acid in the treatment of acute promelocytic leukemia. Aust N. Z. J Med 22: 449–455), cervical cancer (Lippman S. M., et al., 1992 13-cis retinoic acid plus interferon alpha-2a: highly active systemic therapy for squamous cell carcinoma of the cervix. J Natl Cancer Inst 84:241–245), endometrial adenocarcinoma (Kudelka A. P., et al., 1993 Metastatic adenocarcinoma of the endometrium treated with 13-cis retinoic acid plus interferon-alpha. Anticancer Drugs 4:335–337), and squamous cell carcinoma of the skin (Lippman S. M., et al., 1992 13-cis retinoic acid and interferon alpha-2a: effective combination therapy for advanced squamous cell carcinoma of the skin. J Natl Cancer Inst 84: 235–241). Because the complement of retinoid receptor subtype proteins expressed in any particular cell may play an important role in how that cell responds to hormonal stimuli, it will be useful to know the complement of retinoid receptor subtypes in a certain cell or tumor prior to treatment. A therapeutic strategy using subtype-specific retinoid analogues could be developed according to the receptor subtype profile of a particular tumor or cell sample.

This invention describes a method that elicits sensitive and specific detection of the different subtypes of endogenous retinoid receptor proteins in cultured cell lines and tumor samples. In a specific example, this method combines labelling cell extracts with a high affinity tritiated retinoid ligand, competition of tritiated ligand with an excess of unlabelled receptor subfamily-selective ligand, and the immunoprecipitation of these specific counts with a receptor subtype-specific antibody. This approach yields a substantially more accurate, reliable, and sensitive result than either technique provides alone.

Prior to immunoprecipitation, the cell extracts were tested for receptor subfamily complement by a subfamily-specific hormone-binding assay. This assay makes use of high affinity compounds that are RAR-selective (tRA), RXR-selective (LG100268), or bifunctional (9cRA), to determine the presence of RXRs which bind to 9cRA (Allegretto EA, et al., 1993, "Transactivation properties of retinoic acid and retinoid X receptors in mammalian cells and yeast: correlation with hormone binding and effects of metabolism." J Biol Chem 268:26625–26633) and LG100268 with high affinity; RARs which bind to tRA and 9cRA with equally high affinity (Allenby G., et al., 1993, "Retinoic acid receptors and retinoid X receptors: interactions with endogenous retinoic acids." Proc Natl Acad Sci USA 90:30–34; Allegretto E. A., et al., 1993, "Transactivation properties of retinoic acid and retinoid X receptors in mammalian cells and yeast: correlation with hormone binding and effects of metabolism." J Biol Chem 268:26625–26633); and cellular retinoic acid binding proteins (CRABPs) which only bind to tRA (Allenby G., et al., 1993, "Retinoic acid receptors and retinoid X receptors: interactions with endogenous retinoic acids." Proc Natl Acad Sci USA 90:30–34).

The presence of retinoid receptor subtype is determined by use of subtype-selective antibodies in the hormone-binding immunoprecipitation assay. Subtype-specific antipeptide antibodies have been developed against each of the retinoic acid receptors (RARs α, β, γ) and each of the retinoid X receptors (RXRs α, β, γ). Each antibody reacts specifically with its respective recombinantly-expressed protein, but not with any of the other retinoid receptor subtypes, by both immunoblot and immunoprecipitation technology.

The sensitivity of this hormone-binding and immunoprecipitation technique is limited only by the specific activity of the tritiated ligands and by the amount of protein extract that is available. In the following nonlimiting examples, approximately $5\times10^6$ cells or 150 mg tumor are required to perform a complete assay twice. The assay of this invention elicits sensitivity of 5 fmol receptor per mg of total soluble protein. As tritiated retinoids or other retinoid receptor-binding ligands of higher specific activity are developed, lower levels of the less abundant receptors will become detectable by the assay using less protein extract.

These assays have clear ramifications in the development of drug treatment strategies that would utilize retinoid receptor subtype-selective drugs.

The invention will now be described in greater detail by reference to the following non-limiting examples regarding identifying retinoid receptors in cell extracts.

EXAMPLES

Peptide and Antibody Production

Peptides were synthesized, purified, and conjugated to Keyhole Limpet Hemocyanin by standard methods (see, *Antibodies, A Laboratory Manual*, Edttarlow, David Lane, eds., Cold Spring Harbor Laboratory (1988)). Conjugated peptides (10–100 µg) were injected with Freund's complete adjuvant into mice or rabbits, subsequent boosts were done in incomplete adjuvant at monthly intervals, and serum titers were monitored by reaction of sera on Western blots with recombinantly-expressed receptors. Hybridomas against RARα were produced in mice by the standard protocol (Kohler G. and Milstein C. 1975 Continuous cultures of fused cells secreting antibody of predefined specificity. Nature 256:495–497). Rabbit antisera against the other five retinoid receptor subtypes was used for Western blots and immunoprecipitation. Total Immunoglobulin G was purified from the sera for use in immunoprecipitation experiments.

Protein Extract Preparation

The retinoid receptor cDNAs: hRARα (Giguere V., et al., 1987 Identification of a receptor for the morphogen retinoic acid. Nature 330:624–629.), hRARβ (Benbrook D., et al., 1988 A new retinoic acid receptor identified from a hepatocellular carcinoma. Nature 333:669–672.), hRARγ (Ishikawa T., et al., 1990 A functional retinoic acid receptor encoded by the gene on human chromosome 12. Mol Endocrinol 4:837–844.), hRXRα (Mangelsdorf D. J., et al., 1990 Nuclear receptor that identifies a novel retinoic acid response pathway. Nature 345:224–229.), mRXRβ (Mangelsdorf D. J., et al., 1992 Characterization of the three RXR genes that mediate the action of 9-cis retinoic acid. Genes Develop 6:329–344.), and mRXRγ (Mangelsdorf D. J., et al., 1992 Characterization of the three RXR genes that mediate the action of 9-cis retinoic acid. Genes Develop 6:329–344.) were constructed separately into yeast and baculovirus expression vectors as described in detail elsewhere (Allegretto E. A., et al., 1993, "Transactivation properties of retinoic acid and retinoid X receptors in mammalian cells and yeast: correlation with hormone binding and effects of metabolism." J Biol Chem 268:26625–26633).

Cells (yeast or Sf21 insect cells) were harvested, washed, and high salt extract preparations were produced as described previously (Allegretto E. A., et al., 1993, "Transactivation properties of retinoic acid and retinoid X receptors in mammalian cells and yeast: correlation with hormone binding and effects of metabolism." J Biol Chem 268:26625–26633). HeLa S3 (human cervical carcinoma), Hep G2 (human hepatoma), MCF-7 (human breast carcinoma) cells, and HL60 (human promyelocytic leukemia) cells were grown as recommended by the ATCC. MCF-7 cells were transferred into media containing phenol red-free, charcoal-stripped serum for 72 h and were then either untreated or treated with $10^{-8}$ β-estradiol for 6 hours.

The cultured cells were harvested by trypsinization, washed twice in cold PBS and then the cell extracts were prepared as described previously for Sf21 cells (Allegretto E. A., et al., 1993, "Transactivation properties of retinoic acid and retinoid X receptors in mammalian cells and yeast: correlation with hormone binding and effects of metabolism." J Biol Chem 268:26625–26633) except that DTT was used at 1 mM. MCF-7 or ME-180 (human cervical carcinoma) cells were injected into athymic mice (NcR) to form tumors (Giovanella B. C., et al., 1974 Heterotransplantation of human malignant tumors in "nude" thymusless mice. JNCI 52:921–927.). Ovariectomized mice injected with MCF-7 cells received β-estradiol pellets (0.72 mg/8 week release) to initiate tumor formation. Tumors were resected, weighed, rinsed with cold PBS, minced, and extracts were prepared as described previously (Allegretto E. A., et al., 1993, "Transactivation properties of retinoic acid and retinoid X receptors in mammalian cells and yeast: correlation with hormone binding and effects of metabolism." J Biol Chem 268:26625–26633), except that a Polytron homogenizer was used.

Western Blot Analysis

Protein extracts containing recombinant retinoid receptors were subjected to SDS-PAGE, transferred to nitrocellulose, blocked, and washed as described previously (Allegretto E. A., et al 1993, "Transactivation properties of retinoic acid and retinoid X receptors in mammalian cells and yeast: correlation with hormone binding and effects of metabolism." J Biol Chem 268:26625–26633). Blots were incubated overnight at room temperature in primary antibody solutions. Antibody titers were determined (ranging from 1:2000 to 1:100,000) prior to performing cross reactivity studies with the six retinoid receptor proteins. Secondary antibodies conjugated to alkaline phosphatase were then bound and substrate added as described previously (Allegretto E. A., et al., 1993, "Transactivation properties of retinoic acid and retinoid X receptors in mammalian cells and yeast: correlation with hormone binding and effects of metabolism." J Biol Chem 268:26625–26633).

Hormone-binding Assay

Hormone-binding assay conditions were as described previously (Allegretto E. A., et al., 1993, "Transactivation properties of retinoic acid and retinoid X receptors in mammalian cells and yeast: correlation with hormone binding and effects of metabolism." J Biol Chem 268:26625–26633) except that DTT was omitted from the binding buffer. Briefly, recombinant retinoid receptor extracts from yeast or Sf21 sources (20–50 μg) or cultured cell or tumor extracts (500 μg) were incubated with 10 nM [$^3$H]-tRA (~50 Ci/mmol; New England Nuclear) or [$^3$H]-9cRA (29 Ci/mmol; Ligand Pharmaceuticals, Inc.) with and without a 200-fold molar excess of the respective unlabelled retinoid to determine specific binding.

Cultured cell and tumor extracts were labelled with [$^3$H]-9cRA in the presence and absence of a 200-fold molar excess of unlabelled 9cRA to estimate the total counts from both the RAR and RXR subfamilies. Cultured cell and tumor extracts were labelled with [$^3$H]-9cRA in the presence and absence of a 200-fold molar excess of either unlabelled tRA, or LG100268 (a high affinity RXR-selective compound produced and characterized at Ligand Pharmaceuticals, Inc.; International patent application number PCT/US93/03944) to estimate the contribution of the total counts from the RAR and RXR subfamilies, respectively.

Cultured cell and tumor extracts were labelled with [3H]-tRA in the presence and absence of a 200-fold molar excess of unlabelled tRA to estimate the total counts from both the RAR subfamily and CRABPs. Cultured cell and tumor extracts were labelled with [3H]-tRA in the presence and absence of a 200-fold molar excess of unlabelled 9cRA to estimate the total counts from the RAR subfamily.

Methods for labelling ligands (such as tRA and 9cRA) with tritium have been disclosed previously in Kaegi, H. H., et al., J. Labelled Compd. Radiopharm., 18:1099, 1981 and Dawson, M. I., et al., J. Labelled Compd. Radiopharm., 33:245, 1993, incorporated by reference herein.

Immunoprecipitation

Labelling of retinoid receptors with tritiated hormones was allowed to proceed for 5–16 h at 4° C. before purified primary antibodies were added (equivalent amounts of total IgG) for 2 or 16 h at 4° C. Protein A Sepharose (Pharmacia) was added for 1–4 hours at 4° C. rotating end-over-end. The protein A Sepharose pellets were washed twice with high salt binding buffer (0.4 M KCl, 20 mM Tris, pH 7.5, 0.5–0.75% CHAPS), twice with the same buffer containing 0.15 M KCL, and then quantitated for tritium by scintillation counting.

Example 1

Selecting Peptides to Elicit Retinoid Receptor Subtype Specific Antibodies

Peptide sequences from the RARs were chosen based upon their previously determined antigenicity (Gaub MP, et al., 1989 Antibodies specific to the retinoic acid human nuclear receptors alpha and beta. Proc Natl Acad Sci USA 86:3089–3093) and their dissimilarity to each other.

Nonhomologous peptide sequences were chosen from the hinge regions of each of the RXR subtypes. This region is thought to be an exposed area of the receptor since it is extremely susceptible to proteases and is an antigenic region in other intracellular receptors such as the vitamin D receptor (VDR) (Allegretto E. A., et al., 1987 Immunochemical detection of unique proteolytic fragments of the chick 1,25-dihydroxyvitamin D$_3$ receptor. J Biol Chem 262:1312–1319).

TABLE I

| | Retinoid receptor peptide sequences used as antigens | | |
|---|---|---|---|
| Receptor Subtype | Peptide Sequence* | Amino Acid | Region |
| hRARα | GLAPPPGSCSPSC Seq. ID. No. 5 | 436–447 | C-terminus |
| hRARβ-CT | VENSGVSQSPLVQC Seq. ID. No. 6 | 436–448 | C-terminus |
| hRARβ-AT | SPGQILDFYTASPSSC Seq. ID. No. 7 | 11–26 | N-terminus |
| hRARγ | DEVPGGQGKGGLKC | 439–451 | C-terminus |
| hRXRα | QRGKDRNENEVEC Seq. ID. No. 2 | 210–221 | hinge |
| mRXRβ† | QKSDQGVEGPGATC Seq. ID. No. 3 | 190–202 | hinge |
| mRXRγ | RQRSRERAESEAEC Seq. ID. No. 4 | 213–226 | hinge |

*Cysteines that have been added to the natural sequence for KLH conjugation are underlined.
†Corresponding hRXRβ sequence: QKSDQGVEGPGGT

Example 2

Immunoblot Analysis of Recombinant Retinoid Receptor-containing Extracts to Determine Reactivity of the Antibodies Each peptide induced antibody preparation was tested by Western blot analysis for reactivity with each of the retinoid receptor subtypes as well as with VDR and with estrogen receptor (ER).

As demonstrated in FIG. 1, extracts (total soluble protein) from Sf21 cells uninfected (40 μg: A, lane 5; B, lane 8; C, lane 8; D, lane 5; F, lane 5) or infected with recombinant viral expression vectors producing hRARα (40 μg: A–F, lane 2), hRARβ (40 μg: A–F, lane 3; 4 μg: B, lane 4; 0.8 μg, lane 5; 0.4 μg, lane 6), hRARγ (40 μg: A, C–F, lane 4; B, lane 7; 4 μg: C, lane 5; 0.8 μg: C, lane 6; 0.4 μg: C, lane 7) or from yeast strain BJ2168 untransformed (40 µg: B,C, lane 14; D, lane 11) or transformed with hRXRα (40 µg: A,D,F, lane 6; B,C, lane 9; E, lane 5), mRXRγ (40 µg: A,D,F, lane 8; B,C, lane 11; E, lane 10) or hER (40 µg: A,D,F, lane 9; B,C, lane 12; E, lane 11) or yeast strain BJ3505 untransformed (40 µg: B,C, lane 15; D, lane 12; E, lane 13) or transformed with mRXRβ (40 µg: A,D,F, lane 7; B,C, lane 10; E, lane 6; 4 µg: E, lane 7; 0.8 µg: E, lane 8; 0.4 µg: E, lane 9) or hVDR (40 µg: A,D,F, lane 10; B,C, lane 13; E, lane 12) were electrophoresed on SDS-PAGE gels, transferred to nitrocellulose membranes and probed with antibodies against RARα (A), RARβ (B), RARγ (C), RXRβ (D), RXRβ (E), or RXRβ (F). Prestained molecular weight standards (A–F, lane 1; Bio-Rad) were as follows (in daltons): phosphorylase β, 106,000; bovine serum albumin, 80,000; ovalbumin, 49,500; carbonic anhydrase, 32,500; soybean trypsin inhibitor, 27,500; lysozyme, 18,500.

The recombinant receptors are expressed at approximately 0.1–0.5% of the total protein and are detected by this immunoblotting method at ~4–200 ng receptor per lane, depending on the expression level of the particular receptor and the antibody used. Each antibody, while reacting with the recombinantly-expressed receptor containing the peptide from which the antibody was produced, does not react with any of the other retinoid receptor subtypes or with recombinantly-produced VDR or ER. For example, the anti-RARα monoclonal antibody produces an immunoreactive signal of the expected molecular weight, ~50 kDa, with extract containing recombinantly-expressed RARα (FIG. 1A, lane 2) and is unreactive with the extracts containing the other receptors (FIG. 1A, lanes 3–10). Additional immunoreactive bands observed on the blots represent nonspecific interactions, as confirmed by the presence of these bands in extracts from wildtype yeast or Sf21 cells that do not contain the receptor cDNA.

These immunoblotting assays indicate that the antibodies specifically recognize the receptor proteins following SDS-PAGE, most likely representing denatured or partially renatured receptors. Example 3

Immunoprecipitation of Tritiated Hormone-receptor-antibody Complexes

To test whether these peptide elicited antibodies react with retinoid receptors in their native hormone-bound conformation, we employed immunoprecipitation techniques. Extracts were prepared from yeast or Sf21 cells containing the individual recombinantly-expressed retinoid receptors and labelled with [$^3$H]-tRA or [$^3$H]-9cRA. Purified antibodies were then incubated with the labelled extracts. The tritiated hormone-receptor-antibody complexes were precipitated with protein A Sepharose, washed and quantitated by scintillation counting.

As demonstrated in FIG. 2, Sf21 cell extracts (50 µg total soluble protein) containing recombinantly-expressed hRARα (A), hRARβ (B), or hRARγ (C) were labelled with 10 nM [$^3$H]-tRA, then incubated with anti-RARα (A–C: 1 µg, lane 1; 5 µg, lane 2; 25 µg, lane 3), anti-RARβ (A–C: 10 µl, lane 4; 50 µl, lane 5; 100 µl, lane 6), or anti-RARγ (A,B: 10 µl, lane 7; 50 µl, lane 8; 100 µl, lane 9; C: 2 µl, lane 7; 5 µl, lane 8; 20 µl, lane 9) antibodies, then incubated with protein A Sepharose, the pellets were washed, and then counted for tritium. Yeast extracts (50 µg total soluble protein) containing hRXRα (D), mRXRβ (E), or mRXRγ (F) were labelled with 10 nM [$^3$H]-9cRA, then incubated with anti-RXRα (D–F: 10 µl, lane 1; 50 µl, lane 2; 100 µl, lane 3), anti-RXRβ (D–F: 10 µl, lane 4; 50 µl, lane 5; 100 µl, lane 6), anti-RXRγ (D–F: 10 µl, lane 7; 50 µl, lane 8; 100 µl, lane 9), or normal rabbit antibody (E: 10 µl, lane 10; 50 µl, lane 11; 100 µl, lane 12) and then precipitated as above for A–C.

Figure 2A:
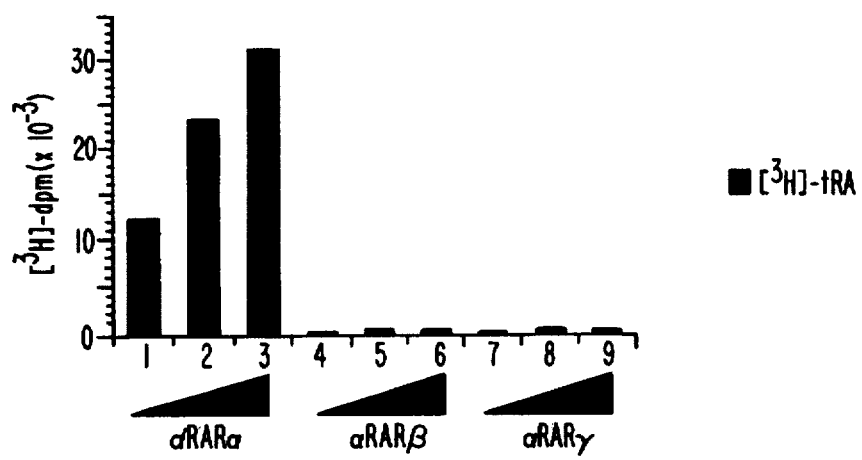
FIG. 2 shows immunoprecipitation of tritiated hormone-receptor complexes with subtype-specific retinoid receptor antibodies. Cell extracts containing a solitary recombinant retinoid receptor were incubated with tritiated hormone ligands and anti-retinoid receptor subtype selective antibodies, precipitated with protein A Sepharose, and pellets were then counted for tritium.
Figure 2B:
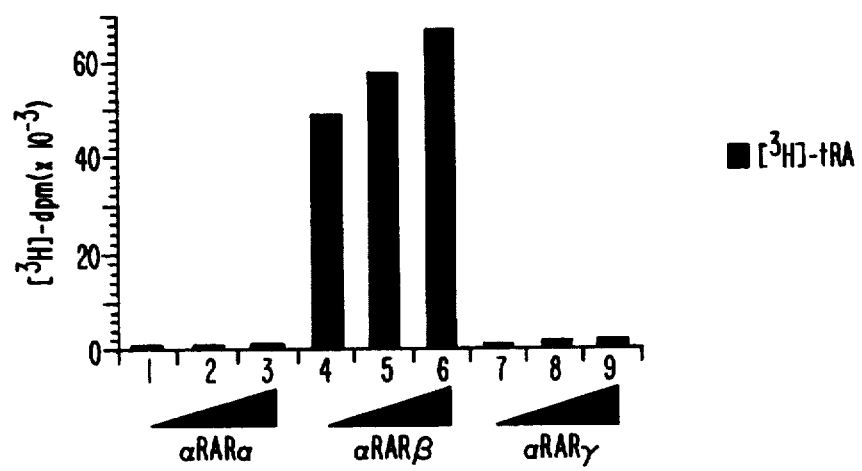
Figure 2C:
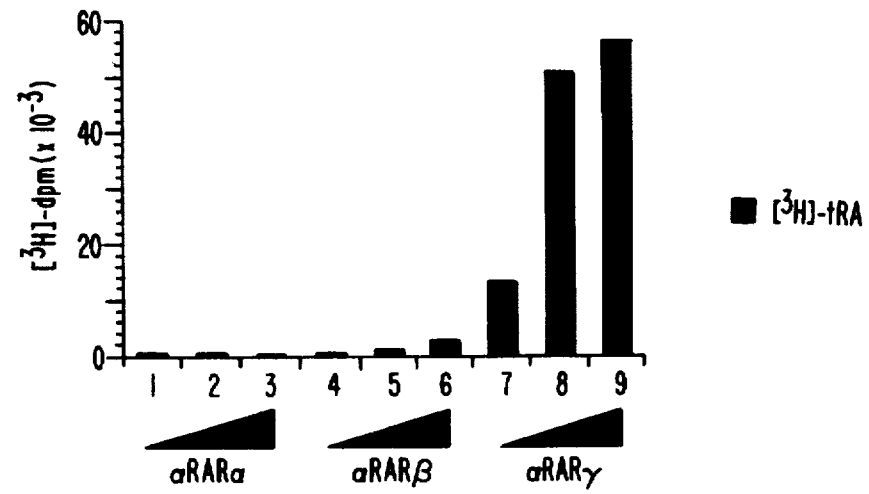
Figure 2D:
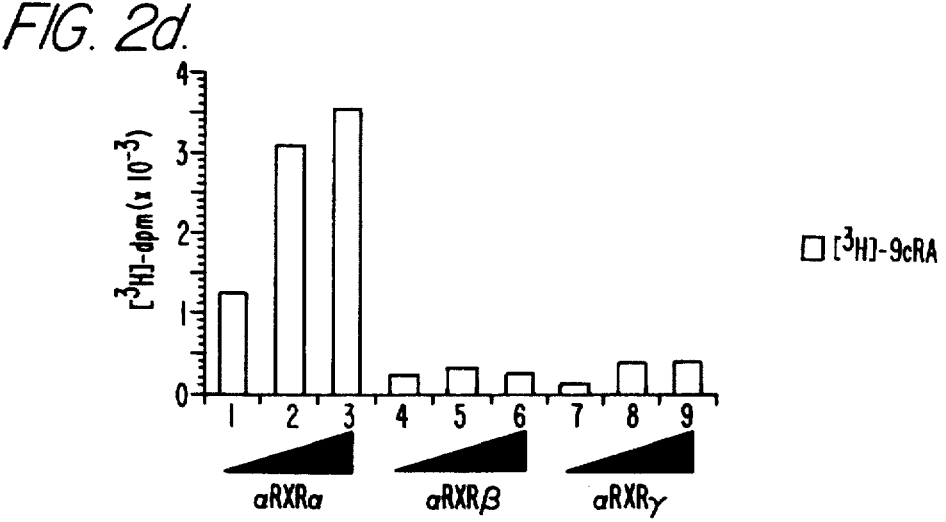
Figure 2E:
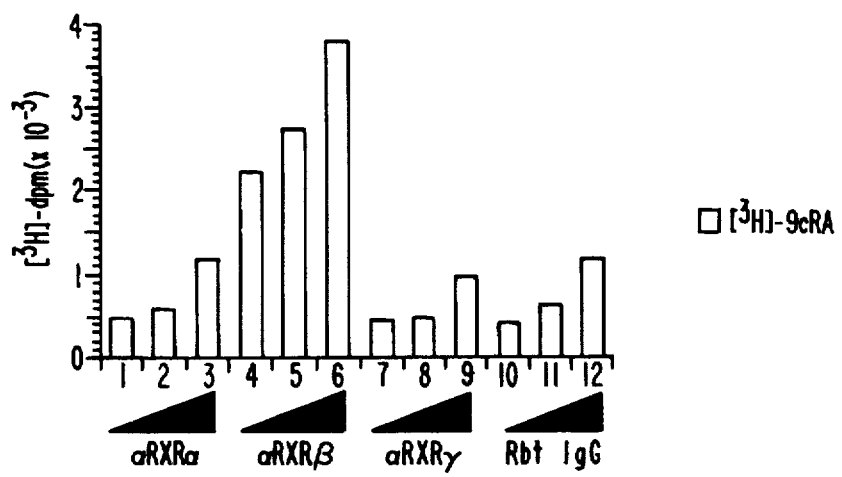
Figure 2F:
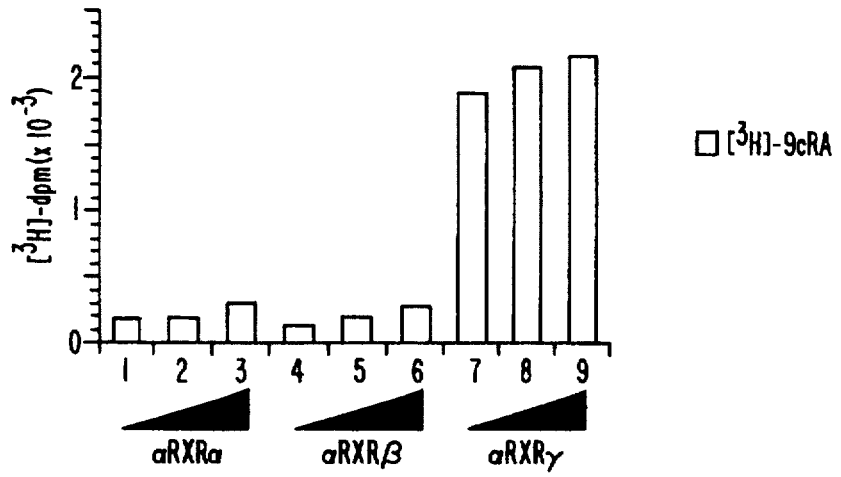

RARα from an Sf21 extract labelled with [$^3$H]-tRA was specifically precipitated with the anti-RARα antibody in an antibody concentration-dependent manner (FIG. 2A, lanes 1–3). This data indicates that this monoclonal antibody reacts with the native hormone-bound RARα. Furthermore, this antibody reacts only with RARα and not with RARβ (FIG. 2B, lanes 1–3) or RARγ (FIG. 2C, lanes 1–3) or with the RXRs. This is evidenced by only a low amount of nonspecific binding of tritium dpm to Sepharose which is not antibody concentration-dependent. Each of the other anti-retinoid receptor antibodies also reacts with their respective native receptors and not with the other receptor proteins in the subfamily (FIG. 2A–F) or in the alternate subfamily.

The RXRs are produced in yeast at a lower level than either they or the RARs are expressed in Sf21 cells, and the tritiated 9cRA that is used to label the RXRs is of lower specific activity than is the tritiated tRA used to label the RARs. Hence, less tritiated dpm is precipitated with the anti-RXR antibodies than with the anti-RAR antibodies.

Immunoprecipitations performed with RXRβ-containing extracts exhibited an increase in precipitated dpm with increasing concentration of anti-RXRα (FIG. 2E, lanes 1–3) and anti-RXRγ (FIG. 2E, lanes 7–9) antibodies. However, this same increase is exhibited with normal rabbit antibody (FIG. 2E, lanes 10–12) and therefore represents nonspecific binding. Likewise, any antireceptor subtype antibody concentration-dependent increases in tritium binding to Sepharose displayed by other extracts not containing that subtype were accounted for as nonspecific binding.

Example 4

Identification of Retinoid Receptor Subfamilies with Hormone-binding Assay

Hormone-binding assays were used to measure the specific binding contribution (and hence, the approximate amounts) of each of the receptor subfamilies in various cultured cell lines and tumor samples.

To measure the endogenous RAR component, cell extracts were incubated with tritiated tRA in the presence and absence of a 200-fold molar excess of unlabelled 9cRA and binding was analyzed by a hydroxylapatite binding assay as described previously (Allegretto E. A., et al., 1993, "Transactivation properties of retinoic acid and retinoid X receptors in mammalian cells and yeast: correlation with hormone binding and effects of metabolism." J Biol Chem 268:26625–26633). Specific binding indicative of the RARs was determined by subtraction of the amount of bound tritium in the presence of excess 9cRA (nonspecific binding) from the amount of tritium bound to hydroxyapatite in the absence of excess 9cRA (total binding). Total RAR was also measured by incubating extracts with tritiated 9cRA in the presence and absence of excess unlabelled tRA and subsequent determination of the specific binding by subtraction of the nonspecific binding from the total binding, as stated above.

To measure the cellular RXR component, cell extracts were incubated with tritiated 9cRA in the presence and absence of a 200-fold molar excess of an unlabelled RXR-selective compound, LG100268. Specific binding indicative of the RXRs was determined by subtracting the nonspecific binding (tritium bound in the presence of an excess of ligand) from the total binding (tritium bound in the absence of unlabelled ligand).

As demonstrated in FIG. 3, extracts (500 µg) from HeLa (A–C) or Hep G2 (D–F) cells were incubated with 10 nM [3H]-tRA (A,D; lanes 1–3) or with 10 nM [3H]-9cRA (A,D; lanes 4–6) in the presence of a 200-fold molar excess of unlabelled tRA (A,D; lanes 1,4), unlabelled 9cRA (A,D; lanes 2,5), or unlabelled LG100268 (A,D; lane 3,6).

As demonstrated in FIG. 4, extracts (500 µg) from untreated MCF-7 cells (A–C) or MCF-7 tumor from estrogen-treated mouse (D–F) were incubated with 10 nM [3H]-tRA (A,D; lanes 1,2) or 10 nM [3H]-9cRA (A,D; lanes 3–5) in the presence of a 200-fold molar excess of unlabelled tRA (A,D; lanes 1,3), unlabelled 9cRA (A,D;lanes 2,4) or unlabelled LG100268 (A,D;lane 5).

Figure 3A:
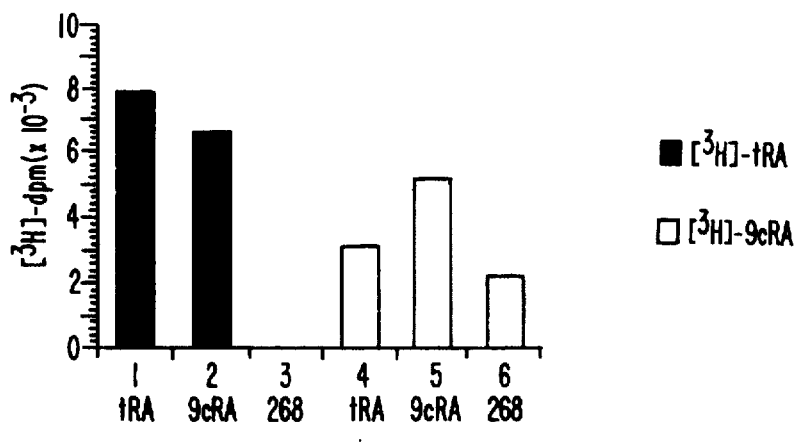
FIG. 3 shows specific binding of HeLa and Hep G2 cell extracts to $[^3H]$-tRA and $[^3H]$-9cRA and immunoprecipitation of receptor-hormone complexes with anti-RAR and anti-RXR antibodies. Extracts from HeLa or Hep G2 cells were incubated with tritiated hormone ligand in an excess of unlabelled ligand to detect specific hormone binding. Hormone bound retinoid receptors were also precipitated by subtype-selective antibodies as in FIG. 2.
Figure 3B:
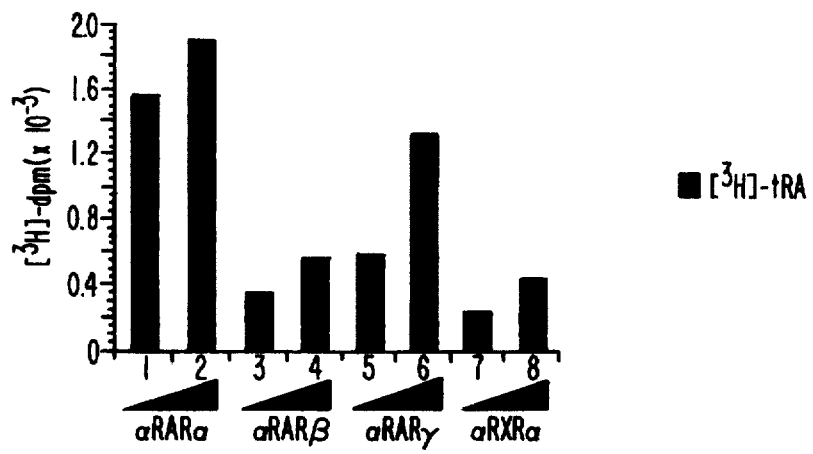
Figure 3C:
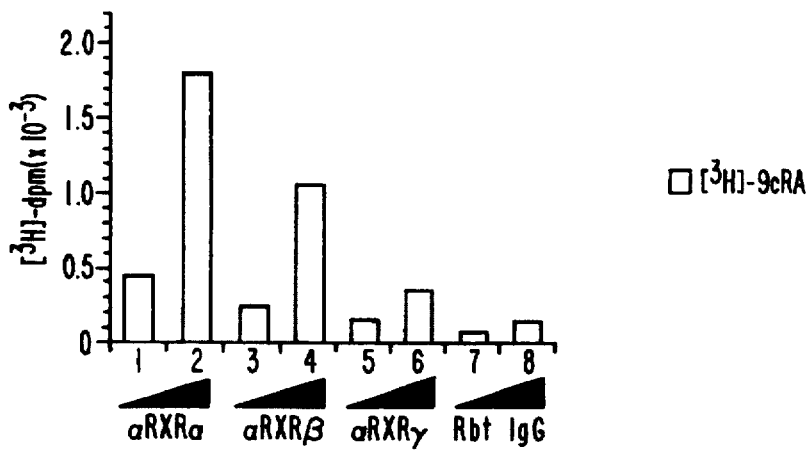
Figure 3D:
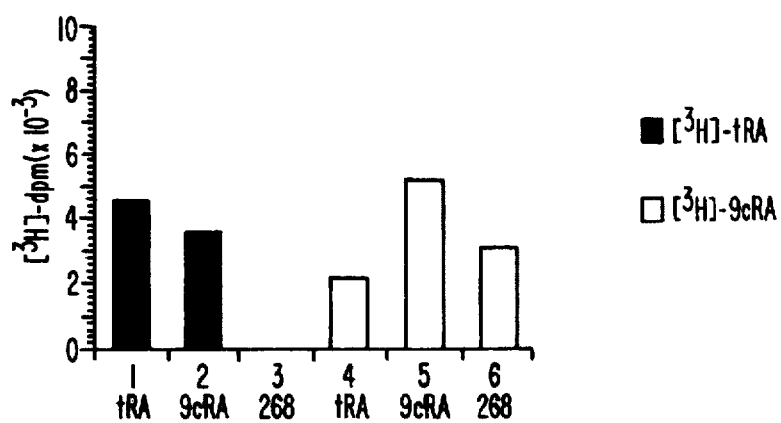
Figure 3E:
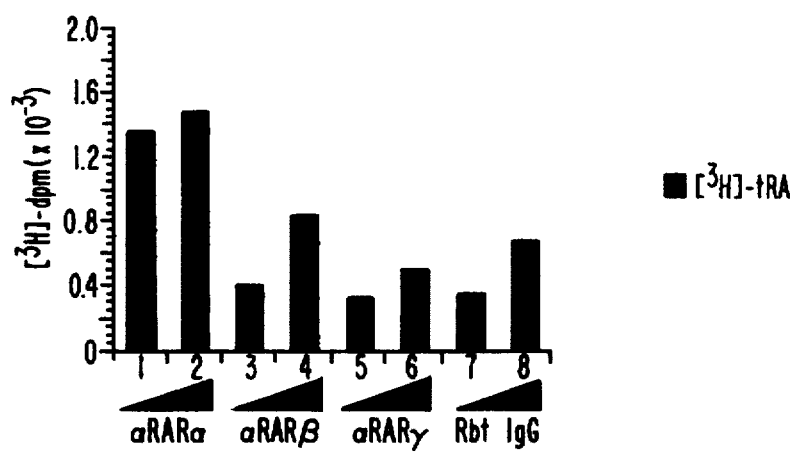
Figure 3F:
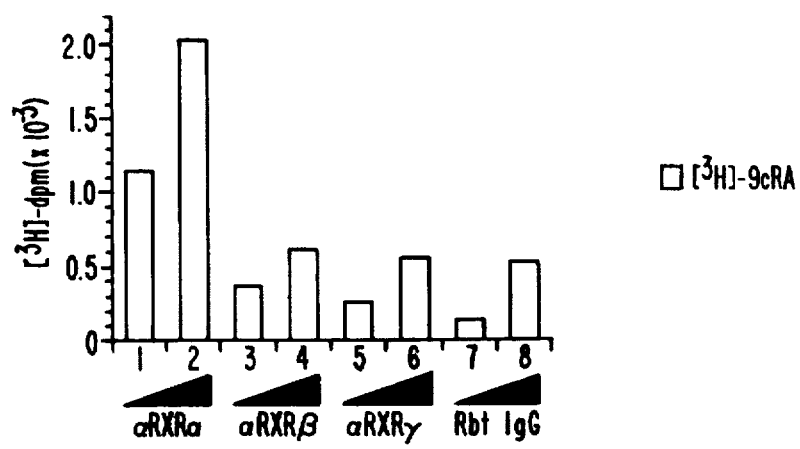
Figure 4A:
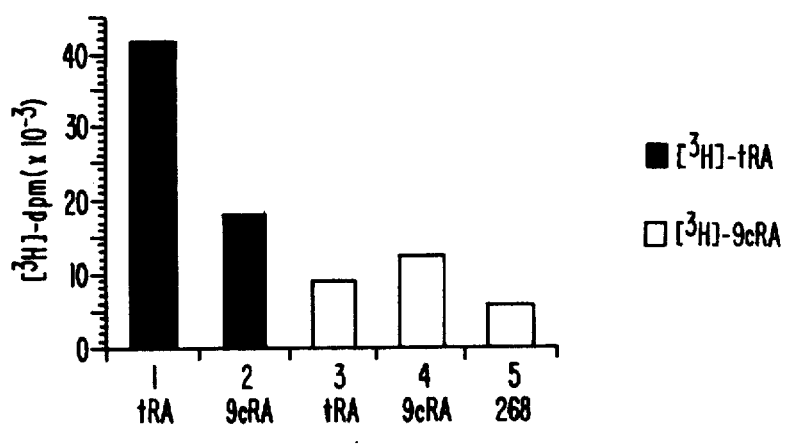
FIG. 4 shows specific binding of MCF-7 cell and MCF-7 tumor extracts to $[^3H]$-tRA and $[^3H]$-9cRA and immunoprecipitation of hormone-receptor complexes with anti-RAR and anti-RXR antibodies. Extracts from untreated MCF-7 cells or MCF-7 tumor from estrogen-treated mouse were incubated with tritiated hormone ligand in an excess of unlabelled ligand to detect specific hormone binding. Hormone bound retinoid receptors were precipitated by subtype selective antibodies as in FIG. 2.
Figure 4B:
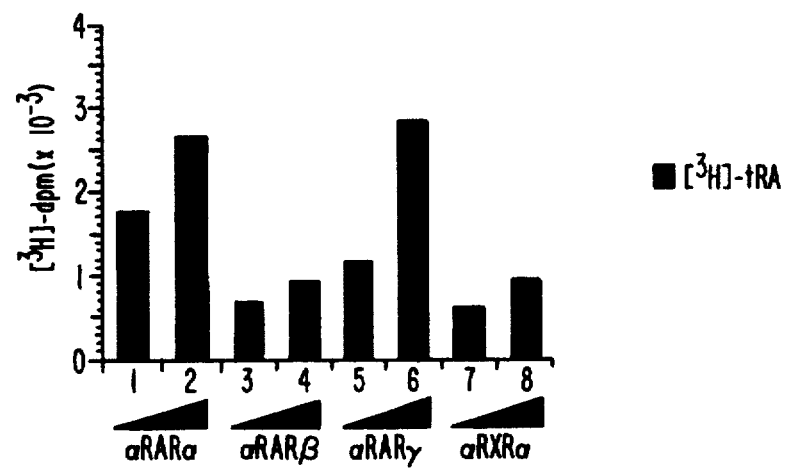
Figure 4C:
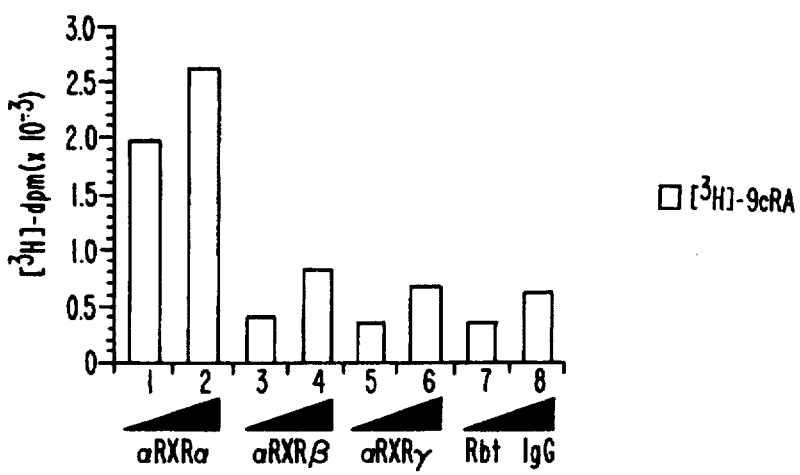
Figure 4D:
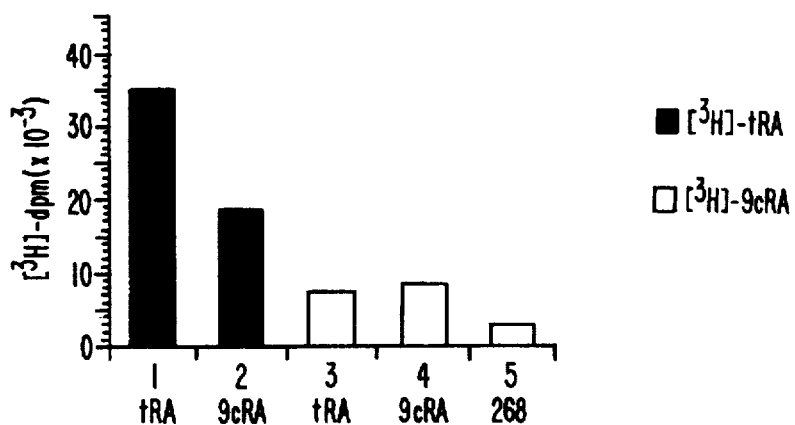

Subfamily-specific hormone-binding assays indicate that both RARs (~100 fmol/mg) and RXRs (~70 fmol/mg) are present in HeLa cells (FIG. 3A; lanes 2,4,6). Hep G2 cell extracts displayed specific binding to [3H]-9cRA which was competed with either excess unlabelled tRA or LG100268, indicating the presence of RARs as well as RXRs (FIG. 3D). MCF-7 cell and MCF-7 cell-derived tumor extracts showed comparable levels of RARs and RXRs as determined by hormone-binding assays (FIG. 4A, 4D).

Example 5

Identification of Retinoid Receptor Subtypes with Immunoprecipitation Assay

Cell lines were tested for their complement of functional (i.e., hormone-binding capable) retinoid receptor subtype proteins. Cell extracts were labelled with [$^3$H]-tRA or [3H]-9cRA. Purified antibodies were then incubated with the labelled extracts. The tritiated hormone-receptor-antibody complexes were precipitated with protein A Sepharose, washen and then quantitated by scintillation counting.

As demonstrated in FIG. 3, extracts (500 µg) from HeLa (B,C) or Hep G2 (E,F) cells were labelled with 10 nM [3H]-tRA (B,E) or 10 nM [$^3$H]-9cRA (C,F), incubated with primary antibodies against RARβ (B,E; 3 µg, lane 1; 10 µg, lane 2), RARβ (B,E; 30 µl, lane 3; 120 µl, lane 4), RARγ (B,E; 30 µl, lane 5; 120 µl, lane 6), RXRα (B; 20 µl, lane 7; 100 µl, lane 8; C,F; 20 µl, lane 1; 100 µl, lane 2), RXRβ (C,F; 20 µl, lane 3; 120 µl, lane 4), RXRγ (C,F; 20 µl, lane 5; 100 µl, lane 6) or with nonspecific rabbit IgG (C,E,F; 0.45 mg, lane 7; 1.8 mg, lane 8) and then precipitated as in FIG. 2.

As demonstrated in FIG. 4, extracts (500 µg) from MCF-7 cells or tumor were labelled with 10 nM [3H]-tRA (B,E) or 10 nM [3H]-9cRA (C,F), and incubated with primary antibodies (amounts as in FIG. 3) against RARα (B,E; lanes 1,2), RARβ (B,E; lanes 3,4), RARγ (B,E; lanes 5,6), RXRα (B; lanes 7,8; C,F; lanes 1,2), RXRβ (C,F; lanes 3,4), RXRγ (C,F; lanes 5,6) or with nonspecific rabbit IgG (C,E,F; lanes 7,8) and then precipitated as in FIG. 2.

HeLa cells were evaluated to verify the assay because hRXRβ is known to be expressed in HeLa cells (Leid M., et al., 1992 Purification, cloning and RXR identity of the HeLa cell factor with which RAR or TR heterodimerizes to bind target sequences efficiently. Cell 68:377–395). FIG. 3B and 3C show that by immunoprecipitation, hormone-bound RARα (~28 fmol/mg), RARβ (~9 fmol/mg), and RARγ (~16 fmol/mg), as well as RXRα (~50 fmol/mg), RXRβ (~28 fmol/mg), and RXRγ (~9 fmol/mg) proteins are evident in HeLa cells. These values are determined by the difference between the tritiated dpm precipitated with the specific antibodies and the dpm precipitated with the same amount of nonspecific antibody.

Additional immunoprecipitation experiments were performed to confirm receptor levels that were determined to be less than 10 fmol/mg. Cell extracts were incubated with tritiated ligand in the presence or absence of a 200-fold molar excess of unlabelled ligand. Receptor subtype presence was determined by the difference between the number of scintillation counts precipitated in the absence of excess unlabelled ligand and that in the presence of excess unlabelled ligand.

Of the cell lines tested herein, only HeLa cells exhibited detectable levels of RXRγ. This result correlates with the report that RXRγ RNA is nondetectable in most tissues and is expressed at extremely low levels in a few tissues, such as heart or muscle (Mangelsdorf D. J., et al., 1992 Characterization of the three RXR genes that mediate the action of 9-cis retinoic acid. Genes Develop 6:329–344).

Hep G2 cells were tested for retinoid receptor complement because liver is an active site for retinoid metabolism (Blomhoff R, et al., 1990 Transport and storage of vitamin A. Science 250:399–404) and has been shown to express retinoid receptor mRNA (Benbrook D, et al., 1988 A new retinoic acid receptor identified from a hepatocellular carcinoma. Nature 333:669–672). RXRα RNA is reportedly abundant in liver tissue (Mangelsdorf D. J., et al., 1992 Characterization of the three RXR genes that mediate the action of 9-cis retinoic acid. Genes Develop 6:329–344). Our results show that Hep G2 cells express RARα (~20 fmol/mg, FIG. 3E), RARβ (~5 fmol/mg, FIG. 3E) as well as RXRα protein (~45 fmol/mg, FIG. 3F).

MCF-7 cells reportedly express RARα RNA (van der Burg B, et al., 1993 Retinoic acid resistance of estradiol-independent breast cancer cells coincides with diminished retinoic acid receptor function. Mol Cell Endocrinol 91:149–157), while MCF-7 cell RXR RNA levels have not been reported in the literature. Immunoprecipitation of untreated MCF-7 cell extracts indicated that MCF-7 cells in culture express RARα (~32 fmol/mg), RARγ (~35 fmol/mg), and RXRα (~60 fmol/mg) (Table II, FIG. 4B).

Figure 4E:
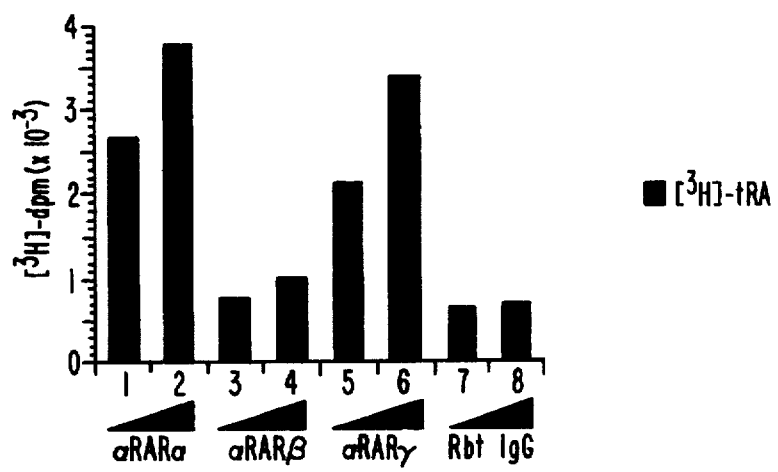
Figure 4F:
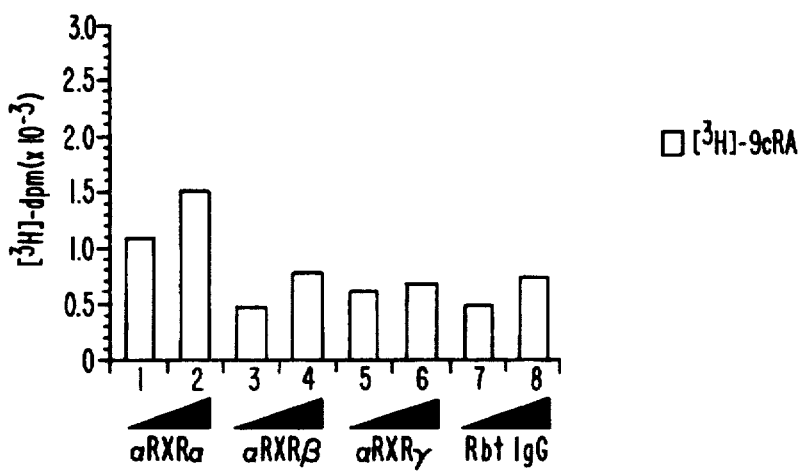

Estrogen treatment of the MCF-7 cells and MCF-7 cell-derived tumors results in the upregulation of RARα protein (~80 and ~57 fmol/mg, respectively, Table II) and the downregulation of RXRα protein (~12 and ~24 fmol/mg, respectively, FIG. 4E). This data is corroborated by immunocytochemistry data with MCF-7 cells which shows that cells that were treated with β-estradiol elicit a more intense fluorescent signal with the RARα monoclonal antibody than do the untreated cells. These findings correlate with a previous study which reported the estrogen-induced upregulation of RARα RNA in another breast cancer cell line, T47D (Roman S. D., et al., 1993 Estradiol induction of retinoic acid receptors in human breast cancer cells. Cancer Res 53:5940–5945. 25. Kohler G and Milstein C 1975 Continuous cultures of fused cells secreting antibody of predefined specificity. Nature 256:495–497).

HL60 cells are interesting because they are known to differentiate upon treatment with tRA and because certain leukemias are currently being treated with retinoic acid (Warrell R. P., et al., 1991 Differentiation therapy of acute promelocytic leukemia with tretinoin (all-trans retinoic acid). N Engl J Med 324:1385–1393; White K. L., et al., 1992 All-trans retinoic acid in the treatment of acute promelocytic leukemia. Aust N. Z. J Med 22:449–455 8). HL60 cells have been reported to express RARα RNA (Daly A. K., et al., 1989 Nuclear retinoic acid binding proteins and receptors in retinoic acid responsive cell lines. Exp Cell Biol 57:339–345; Largman C., et al., 1989 Expression of retinoic acid receptor alpha mRNA in human leukemia cells. Blood 74:99–102) and some groups report the detection of RARβ RNA in HL60 cells (Hashimoto Y., et al., 1990 Expression of retinoic acid receptor genes and the ligand-binding selectivity of retinoic acid receptors (RARs). Biochem Biophys Res Comm 166:1300–1307) while others report it as undetectable (Daly A. K., et al., 1989 Nuclear retinoic acid binding proteins and receptors in retinoic acid responsive cell lines. Exp Cell Biol 57:339–345). Additionally, HL60 cell extracts have been labelled with [$^3$H]-tRA and analyzed via sucrose density gradient centrifugation which indicated that RAR protein(s) are present in HL60 cells, although the technique did not identify which subtype(s) was present (Daly A. K., et al., 1989 Nuclear retinoic acid binding proteins and receptors in retinoic acid responsive cell lines. Exp Cell Biol 57:339–345; Nervi C., et al., 1989 Identification and characterization of nuclear retinoic acid-binding activity in human myeloblastic leukemia HL-60 cells. Proc Natl Acad Sci USA 86:5854–5858).

The immunoprecipitation assay (Table II) showed that HL60 cells have detectable protein levels of RARα (30 fmol/mg). The subfamily-specific hormone-binding assays demonstrated that detectable levels of RXRs are also present in HL60 cells. Immunoprecipitation confirms that RXRα protein is present in these cells at ~60 fmol/mg (Table II).

ME-180 human cervical carcinoma cell-derived tumor extracts contain ~7 fmol/mg RARα and ~30 fmol/mg of both RARγ and RXRβ proteins (Table II).

TABLE II

| Source | Retinoid receptor subtype protein levels in various cultured cell and tumor extracts | | | | |
|---|---|---|---|---|---|
| | RARα | RARβ | RARγ | RXRα | RXRβ |
| RXRγ | | | | | |
| HL60 cells | 30* | ND† | ND | 60 | ND |
| ND | | | | | |
| HeLa cells | 28 | 9‡ | 16 | 50 | 28 |
| 9 | | | | | |
| Hep G2 cells | 20 | 5 | ND | 45 | ND |
| ND | | | | | |
| MCF-7 cells − βE$_2$ | 32 | ND | 35 | 60 | ND |
| ND | | | | | |
| MCF-7 cells + βE$_2$ | 80 | ND | 34 | 12 | ND |
| ND | | | | | |
| MCF-7 tumor + βE$_2$ | 57 | ND | 49 | 24 | ND |
| ND | | | | | |
| ME-180 tumor | 7 | ND | 28 | 30 | ND |
| ND | | | | | |

*fmol receptor/mf protein, values were the mean of at least two experiments, variation was within 15%
†ND: not detected
‡values under 10 fmol/mg were confirmed by immunoprecipitation of extracts incubated with tritiated ligand in the absence and presence of a 200-fold excess of unlabelled ligand.

All publications referenced are hereby incorporated by reference herein, including the nucleic acid sequences and amino acid sequences listed in each publication.

Other embodiments are within the following claims.

What is claimed is:

1. An antibody that binds both to
   (i) an RXRγ, and
   (ii) a peptide of no more than 30 amino acid residues and no less than 8 amino acid residues, comprising a segment of a hinge region of said RXRγ.

2. The antibody of claim 1, wherein said peptide consists of 12 amino acid residues.

3. The antibody of claim 1, wherein said RXRγ is complexed to a ligand.

4. The antibody of claim 1, wherein said antibody is a monoclonal antibody.

5. The antibody of claim 1, wherein said antibody is a polyclonal antibody.

6. The antibody of claim 1, wherein said peptide comprises an amino acid residue sequence RQRSRERAESE-AEC Seq. ID. No. 4.

7. The antibody of claim 1, wherein said peptide consists of RQRSRERAESEAEC Seq. ID. No. 4.

8. Method for detection of RXRγ, comprising the steps of:
   contacting a sample with an antibody, wherein said antibody binds both to (i) an RXRγ, and (ii) a peptide of no more than 30 amino acid residues and no less than 8 amino acid residues, comprising a segment of a hinge region of said RXRγ; and
   detecting a complex formed between said antibody and a constituent of said sample; wherein the detection of said complex is indicative of said RXRγ in said sample.

9. The method of claim 8, wherein said RXRγ is complexed to a ligand.

10. The method of claim 8, wherein said antibody is a monoclonal antibody.

11. The method of claim 8, wherein said antibody is a polyclonal antibody.

* * * * *

UNITED STATES PATENT AND TRADEMARK OFFICE
CERTIFICATE OF CORRECTION

PATENT NO. : 5,585,244
DATED : December 17, 1996
INVENTOR(S) : Elizabeth A. Allegretto et al.

It is certified that error appears in the above-identified patent and that said Letters Patent is hereby corrected as shown below:

Column 2, line 42, delete "RARe" and insert --RARα--

Column 5, line 67, delete "RXR₇" and insert --RXRγ--

Column 11, line 12, delete "RXRβ (D)" and insert --RXRα (D)--

Column 11, line 12, delete "RXRβ (F)" and insert --RXRγ (F)--

Column 13, line 3, delete "[3H]" and insert --[$^{3}$H]--

Column 13, line 3, delete "[3H]" and insert --[$^{3}$H]--

Column 13, line 9, delete "[3H]" and insert --[$^{3}$H]--

Column 13, line 10, delete "[3H]" and insert --[$^{3}$H]--

Column 13, line 17, delete "[3H]" and insert --[$^{3}$H]--

Column 13, line 31, delete "[3H]" and insert --[$^{3}$H]--

Column 13, line 40, delete "RARβ" and insert --RARα--

UNITED STATES PATENT AND TRADEMARK OFFICE
CERTIFICATE OF CORRECTION

PATENT NO. : 5,585,244
DATED : December 17, 1996
INVENTOR(S) : Elizabeth A. Allegretto et al.

It is certified that error appears in the above-identified patent and that said Letters Patent is hereby corrected as shown below:

Column 13, line 48, delete "[3H]" and insert --[$^3$H]--

Column 13, line 49, delete "[3H]" and insert --[$^3$H]--

Column 15, line 31, delete "RXRβ" and insert --RXRα--

Column 16, line 21, delete "mf" and insert --mg--

Signed and Sealed this

Twenty-seventh Day of January, 1998

Attest:

BRUCE LEHMAN

Attesting Officer

Commissioner of Patents and Trademarks